United States Patent
Chen et al.

(10) Patent No.: US 11,318,176 B2
(45) Date of Patent: May 3, 2022

(54) TOPICAL COMPOSITION, PHARMACEUTICAL COMPOSITION CONTAINING INACTIVATED CULTURE AND METHOD OF FACILITATING WOUND HEALING AND SCAR REDUCTION USING THE SAME

(71) Applicant: GenMont Biotech Incorporation, Tainan (TW)

(72) Inventors: Yi-Hsing Chen, Tainan (TW); Wan-Hua Tsai, Kaohsiung (TW); Wen-Wei Chang, Taichung (TW); Chia-Hsuan Chou, Tainan (TW)

(73) Assignee: GenMont Biotech Incorporation, Tainan (TW)

( * ) Notice: Subject to any disclaimer, the term of this patent is extended or adjusted under 35 U.S.C. 154(b) by 175 days.

(21) Appl. No.: 16/539,450

(22) Filed: Aug. 13, 2019

(65) Prior Publication Data
US 2020/0054694 A1 Feb. 20, 2020

(30) Foreign Application Priority Data
Aug. 14, 2018 (CN) .......................... 201810924054.5

(51) Int. Cl.
A61P 17/02 (2006.01)
A61K 35/747 (2015.01)
A61K 9/00 (2006.01)
A61L 15/36 (2006.01)

(52) U.S. Cl.
CPC .......... *A61K 35/747* (2013.01); *A61K 9/0014* (2013.01); *A61L 15/36* (2013.01); *A61P 17/02* (2018.01)

(58) Field of Classification Search
CPC ...... A61K 9/0014; A61K 35/747; A61P 17/02
USPC ........ 424/9.1, 9.2, 93.1, 93.45, 234.1, 246.1
See application file for complete search history.

(56) References Cited

U.S. PATENT DOCUMENTS

2017/0021011 A1 1/2017 Kovarik et al.
2018/0256651 A1 9/2018 Chen et al.

FOREIGN PATENT DOCUMENTS

| CN | 103502434 A | 1/2014 |
|---|---|---|
| CN | 110680836 A | 1/2014 |
| CN | 104017746 A | 9/2014 |
| CN | 104824548 A | 8/2015 |
| CN | 104955437 A | 9/2015 |
| CN | 105189732 A | 12/2015 |
| CN | 105517453 A | 4/2016 |
| CN | 106029100 A | 10/2016 |
| CN | 106727268 A | 5/2017 |
| CN | 107095292 A | 8/2017 |
| CN | 107129534 A | 9/2017 |
| CN | 107137628 A | 9/2017 |
| CN | 107227280 A | 10/2017 |
| CN | 107279286 A | 10/2017 |
| CN | 107281228 A | 10/2017 |
| CN | 108570423 A | 9/2018 |
| CN | 108624520 A | 10/2018 |
| EP | 1 644 492 | 5/2005 |
| EP | 1 604 647 A1 | 12/2005 |
| KR | 20140127437 A | 11/2014 |
| TW | I607758 B | 12/2017 |
| WO | WO 2012/118799 A2 | 9/2012 |
| WO | WO 2017/063909 A1 | 4/2017 |
| WO | WO 2018/187838 A1 | 10/2018 |

OTHER PUBLICATIONS

Darby et al., "Fibroblasts and myofibroblasts in wound healing", Clinical, Cosmetic and Investigational Dermatology, 2014:7, 301-311.

Gerharz et al., "Morphometric analysis of murine skin wound healing: Standardization of experimental procedures and impact of an advanced multitissue array technique", Wound Rep Reg (2007) 15 105-112.

Inoue et al., "Collagenase Expression Is Rapidly Induced in Wound-Edge Keratinocytes After Acute Injury in Human Skin, Persists During Healing, and Stops at Re-Epithelialization", The Journal of Investigative Dermatology, vol. 104, No. 4, Apr. 1995, pp. 479-483, The Society for Investigative Dermatology, Inc.

Nasrabadi et al., "Study of cutaneous wound healing in rats treated with *Lactobacillus plantarum* on days 1, 3, 7, 14 and 21", African Journal of Pharmacy and Pharmacology, vol. 5 (21), pp. 2395-2401-Dec. 6, 2011, Available online at http://www.academicjournals.org/AJPP.

Peral et al., "Bacteriotherapy with *Lactobacillus plantarum* in burns", The Authors. Journal Compilation, Blackwell Publishing Ltd. and Medicalhelplines.com Inc., International Wound Journal, vol. 6, No. 1, 2009, pp. 73-81.

Thiruvoth et al., "Current concepts in the physiology of adult wound healing", Plastic and Aesthetic Research, vol. 2, Issue 5, Sep. 15, 2015, pp. 250-256.

Valdez et al., "Interference of *Lactobacillus plantarum* with *Pseudomonas aeruginosa* in vitro and in infected burns: the potential use of probiotics in wound treatment", Clinical Microbiology and Infection (CMI), vol. 11, No. 6, Jun. 2005, pp. 472-479, European Society of Clinical Microbiology and Infectious Diseases.

Zahedi et al., "Comparison of the effects of *Lactobacillus brevis* and *Lactobacillus plantarum* on cutaneous wound healing in rats", African Journal of Microbiology Research, vol. 5(24), pp. 4226-4233, Oct. 30, 2011, Available online http://www.academicjournals.org/ajmr.

(Continued)

*Primary Examiner* — Patricia Duffy
(74) *Attorney, Agent, or Firm* — Fay Sharpe LLP

(57) ABSTRACT

The present invention relates to a topical composition of facilitating wound healing and reducing scars, which includes an inactivated culture of *Lactobacillus* species as an effective ingredient and can significantly facilitate wound healing as well as reducing scars, thereby can be applied to a method of facilitating wound healing and reducing scars.

3 Claims, 5 Drawing Sheets
(3 of 5 Drawing Sheet(s) Filed in Color)
Specification includes a Sequence Listing.

(56) References Cited

OTHER PUBLICATIONS

Christos G. Tsiouris et al., "The efficacy of probiotics as pharmacological treatment of cutaneous wounds: Meta-analysis of animal studies" European Journal of Pharmaceutical Sciences, vol. 104, Apr. 7, 2017, pp. 230-239.

Fu Shuai et al., "Clinical value of recombinant human epidermal growth factor on the wound healing after cesarean section" Journal of Tropical Medicine, vol. 15, No. 1, Jan. 2015, pp. 59-61.

Zhuang Hai-Ji et al., "Progress in Application of Lactobacillus paracasei" Letters in Biotechnology, vol. 17, No. 6, Nov. 2006, pp. 989-991.

Jia Mutai et al., "Characteristics of antimicrobial substance produced by Lactobacillus paracasei" CHINA Dairy Industry, vol. 46, No. 2, 2018, pp. 9-15.

Zahedi, F. et al., "The effect of Lactobacillus brevis isolated from Iranian traditional cheese on cutaneous wound healing in rats" Journal of Cell and Animal Biology, vol. 5(12), Oct. 30, 2011, pp. 265-270.

TOPICAL COMPOSITION, PHARMACEUTICAL COMPOSITION CONTAINING INACTIVATED CULTURE AND METHOD OF FACILITATING WOUND HEALING AND SCAR REDUCTION USING THE SAME

RELATED APPLICATION

This application claims priority to China Application Serial Number 201810924054.5, filed on Aug. 14, 2018, which is herein incorporated by reference in its entirety.

BACKGROUND

Field of Invention

The present invention relates to a topical composition. More particularly, the present invention relates to a topical composition using an inactivated culture of Lactobacillus species and the method of facilitating wound healing and scars reduction using the same.

Description of Related Art

The process of wound healing is generally divided into four phases. Hemostasis phase, the first phase of wound healing, begins at the onset of wound till the bleeding stops. Inflammatory phase, the second phase, is often associated with inflammatory responses including slightly erythema, edema, heat and pain of the wound, which is caused by the human immune system defense response against infection of foreign bacteria and microorganisms.

During the proliferative phase, the third phase, new capillaries gradually form in the wound bed and bring more collagen matrix to fill the wound. Granulation tissues also proliferate in this stage, in which fibroblasts are activated, thereby expressing α-smooth muscle actin (α-SMA) and transforming into myofibroblasts. The myofibroblasts have de novo extracellular matrix (ECM) materials and are capable of scar contracting, thereby causing the wound to close gradually.

Maturation phase, or remodeling phase, is the fourth phase when redundant capillaries degenerate and atrophy after the wound is closed and healed. The collagen matrix elongates as well as neatly arranges, and the scar becomes flat and thin.

In the process of wound healing, a transformation of the fibroblasts into the myofibroblasts is essential for wound healing. However, during the remodeling phase, improper scabs and fibrosis form if myofibroblasts are excessively activated, resulting in scars. Therefore, the key to preventing the wound from incomplete healing or forming a scar is to regulate the myofibroblasts from excessively activated. A currently known important factor for myofibroblast activation is transforming growth factor-beta (TGF-β). Thus, how to properly regulate TGF-β expression becomes one of the key points for wound healing and scars reduction.

Probiotics have been used for a long time, which is safe without side effect, and previous research has found that topically covering an activated culture of Lactobacillus plantarum on a wound of a burned-mouse can enhance the phagocytosis of the immune cells topically, decrease amounts of pathogens and improve tissue repair. A further study has also found that topically administering Lactobacillus plantarum can decrease the bacteria numbers on a wound of a burn patient and accelerate wound healing clinically. Moreover, an activated culture liquid of Lactobacillus plantarum or Lactobacillus brevis screened according to high production of exopolysaccharide (EPS) can facilitate wound healing of rats. However, without experimental evidence, it is unpredictable whether the probiotics of different strains can facilitate wound healing.

In the view of above, it is necessary to provide a topical composition containing inactivated bacterial culture so as to promote the application of probiotics in wound dressing.

SUMMARY

Therefore, one aspect of the present invention provides a topical composition containing an inactivated culture of Lactobacillus species (sp.) as an effective ingredient, which facilitates wound healing and reduces scars.

Another aspect of the present invention provides a pharmaceutical composition containing an inactivated culture of Lactobacillus sp. as an effective ingredient, which facilitates wound healing and reduces scars. Another aspect of the present invention provides a pharmaceutical composition containing an inactivated culture of Lactobacillus sp. as an effective ingredient, which facilitates wound healing and reduces scars.

The other aspect of the present invention provides a method of facilitating wound healing and reducing scars using an inactivated culture of Lactobacillus sp. originated from Lactobacillus paracasei GMNL-653, and the inactivated culture of Lactobacillus sp. includes an inactivated bacterial culture solution and/or a bacterial lyophilized powder for facilitating wound healing and reducing scars.

According to the aforementioned aspect of the present invention, the pharmaceutical composition of facilitating wound healing and reducing scars is provided, which includes the inactivated culture of Lactobacillus sp. as the effective ingredient. In the embodiment, the inactivated culture of Lactobacillus sp. can be originated from Lactobacillus paracasei GMNL-653, for example, which is deposited with an accession number of CCTCC M2016226 on Apr. 25, 2016 in China Center for Type Culture Collection (CCTCC), Wuhan University, Wuhan 430072, China.

In one embodiment of the present invention, the aforementioned inactivated culture of Lactobacillus sp. includes the inactivated bacterial culture solution and/or a bacterial lyophilized powder.

According to another aspect of the present invention, a pharmaceutical composition of facilitating wound healing and reducing scars includes the inactivated culture of Lactobacillus sp. as an effective ingredient.

In one embodiment of the present invention, an effective dosage of the aforementioned inactivated culture of Lactobacillus sp., for example, can be $1\times10^9$ cells/mL to $1\times10^{10}$ cells/mL.

In one embodiment of the present invention, a dosage form of the aforementioned pharmaceutical composition is selected from the group consisting of a gel, a gel dressing, a spongy dressing, a film dressing or any combination thereof.

According to the other aspect of the present invention, a method of facilitating wound healing and reducing scars using an inactivated culture of Lactobacillus sp. is provided, in which the inactivated bacterial culture can be originated from Lactobacillus paracasei GMNL-653 (the accession number: CCTCC M2016226), for example, and the inactivated bacterial culture includes the inactivated bacterial culture solution and/or the bacterial lyophilized powder.

By applying the topical composition of facilitating wound healing and reducing scars of the present invention, which includes the inactivated culture of *Lactobacillus* sp. as the effective ingredient, wound healing can be facilitated and scars can be reduced significantly, and thus, the invention can further be applied to a method of facilitating wound healing and reducing scars.

BRIEF DESCRIPTION OF THE DRAWINGS

The patent or application file contains at least one drawing executed in color. Copies of this patent or patent application publication with color drawings will be provided by Office upon request and payment of the necessary fee. The invention can be more fully understood by reading the following detailed description of the embodiment, with reference made to the accompanying drawings as follows.

DETAILED DESCRIPTION

Figure 1A:
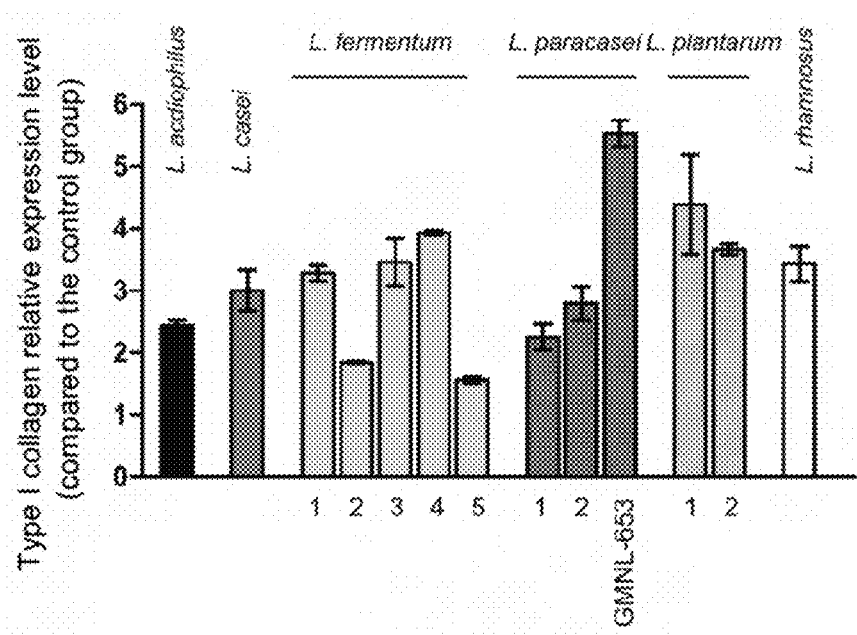
FIG. 1A shows a bar diagram of the type I collagen relative expression level of the human HS68 fibroblasts after treated with the inactivated bacterial culture solutions of different lactic acid bacteria (LAB) strains in accordance with one embodiment of the present invention.

Singular forms, "a", "an", and "the", as mentioned in the present invention also cover plural references, unless otherwise stated in the context. A value range (such as 10% to 11% of A) includes its upper and lower limits (i.e. $10\% \leq A \leq 11\%$) if not otherwise stated specially; the value range, for which if no lower limit is defined (such as B lower than 0.2%, or B below 0.2%), can have a lower limit of zero (i.e. $0\% \leq B \leq 0.2\%$). The aforementioned terms were used for illustrating and helping understand the present invention rather than limiting the scope thereof.

The present invention provides a topical composition of facilitating wound healing and reducing scars, which includes an inactivated culture of *Lactobacillus* species (sp.) as an effective ingredient and can significantly facilitate wound healing and reducing scars.

In one embodiment, the aforementioned inactivated culture of *Lactobacillus* sp. is originated from *Lactobacillus paracasei* GMNL-653. In particular, the aforementioned *Lactobacillus paracasei* GMNL-653 is deposited with an accession number of CCTCC M2016226 on Apr. 25, 2016 in China Center for Type Culture Collection (CCTCC), Wuhan University, Wuhan 430072, China.

In the aforementioned embodiment, the aforementioned inactivated culture of *Lactobacillus* sp. includes an inactivated bacterial culture solution and/or a bacterial lyophilized powder. In some examples, the aforementioned inactivated bacterial culture solution can be made by conventional sterilizations, such as chemical sterilization (e.g., ozone treatment or ethylene oxide gas treatment) or physical sterilization (e.g., ultraviolet light irradiation treatment, ionizing radiation treatment, autoclave or the like). In another example, the aforementioned bacterial lyophilized powder can be made by conventional dehydrating methods, for example, treating the inactivated bacterial culture solution with heat drying or with vacuum lyophilization or spray drying.

In application, the aforementioned inactivated culture of *Lactobacillus* sp. can be applied to a method of facilitating wound healing and reducing scars. In an embodiment of applying the aforementioned inactivated culture of *Lactobacillus* sp. as the topical composition, the topical composition can be an external skin care composition. In an embodiment of applying the aforementioned inactivated culture of *Lactobacillus* sp. as a pharmaceutical composition, the aforementioned pharmaceutical composition can include the inactivated culture of *Lactobacillus* sp. with an effective dosage of $1 \times 10^9$ cells/mL to $1 \times 10^{10}$ cells/mL. In one example, the aforementioned pharmaceutical composition can be topically applied to a test part in ways of covering, wrapping or the like. Therefore, an applicable dosage form can be selected from the group consisting of a gel, a gel dressing, a spongy dressing, a film dressing or any combination thereof, for example.

In the aforementioned embodiment, there is no special restriction for a carrier used in the aforementioned dosage form as long as it does not affect the efficacy of the inactivated culture of *Lactobacillus* sp. In some examples, concrete examples of the aforementioned carrier can include but be not limited to water, polymer and/or moisturizer, etc. A specific example of the aforementioned polymer can include but be not limited to xanthan gum. A specific example of the aforementioned moisturizer can include but be not limited to xylitol, trehalose and/or glycerol, etc.

Animal experiments have proved that the aforementioned topical composition including the inactivated culture of *Lactobacillus* sp. has shown the efficacy of facilitating wound healing and reducing scars. In an example, the aforementioned efficacy of facilitating wound healing can include but be not limited to increasing gene and protein expression levels of a matrix metalloproteinase-1 (MMP-1) in an early stage of wound healing and type I collagen in a middle stage and a late stage of wound healing, so as to accelerate wound healing.

In other examples, the aforementioned efficacy of reducing scars can include but be not limited to inhibiting a transforming growth factor-beta (TGF-β)-induced phosphorylation of Smad-2 and a TGF-β-induced α-smooth muscle actin (α-SMA) overexpression, thereby regulating or preventing forming scars.

Since the aforementioned topical composition including the inactivated culture of *Lactobacillus* sp. is in a dosage form of inactivated bacterial culture, there are no viable cell count as well as deterioration problems, and stability can be controlled more easily. Therefore, the aforementioned pharmaceutical composition can be applied to a method of facilitating wound healing and reducing scars.

The application of the present invention is illustrated by using the following embodiments, but these embodiments should not be considered as limiting the present invention. Various modification and changes can be made by one of ordinary skills in the art to which the present invention pertains, without departing from the spirit and scope of the present invention.

Example 1. Screening of Lactic Acid Bacteria (LAB) for Facilitating Collagen Secretion and MMP-1 Gene Expression of Human Skin Fibroblasts 1. Preparing Inactivated Cultures of LAB In this embodiment, 13 testing bacterial strains, which were 1 strain of *Lactobacillus acidophilus*, 1 strain of *Lactobacillus casei*, 5 strains of *Lactobacillus fetmentum*, 3 strains of *Lactobacillus paracasei* (including GMNL-653 and other 2 strains), 2 strains of *Lactobacillus plantarum* and 1 strain of *Lactobacillus rhamnosus* were selected for performing subsequent tests. The testing bacterial strains were cultured overnight, washed twice with sterile water, adjusted to a cell density of $1\times10^{10}$ cells/mL, autoclaved (121° C.) for 15 minutes, and then prepared as inactivated bacterial culture solutions.

The aforementioned *Lactobacillus paracasei* GMNL-653 was deposited with an accession number of CCTCC M2016226 on Apr. 25, 2016 in China Center for Type Culture Collection (CCTCC), Wuhan University, Wuhan 430072, China. *Lactobacillus paracasei* GMNL-653 was also deposited with an accession number of BCRC 910721 on Feb. 26, 2016 in Bioresource Collection and Research Center (BCRC), Food Industry Research and Development Institute, Hsinchu 30062, Taiwan.

2. Establishment of Cell Model for Assays

Human skin HS68 fibroblasts (CCTCC accession number: GDC403, America Type Culture Collection, ATCC accession number: CRL-1635 or Bioresource Collection and Research Center, BCRC accession number: 60038) were inoculated in 6-well plates ($2\times10^5$ cells/well), cultured overnight, washed twice with phosphate buffered saline (PBS), and then cultured in a serum-free culture medium. The fibroblasts of the experimental groups were treated with the inactivated bacterial culture solutions (in which the concentration were $1\times10^9$ cells/mL, equal to $2\times10^5$ cells/well) of each strain for 24 hours, and those of the control group were treated with the sterile water of a volume equal to that of the inactivated bacterial culture solutions for 24 hours. Then, supernatants were collected and diluted ten-fold into a diluting buffer, followed by analysis with a commercially available enzyme immunoassay (EIA) kit for type I procollagen C-peptide enzyme immunoassay (e.g., Procollagen type I C-peptide EIA kit; Takara Bio Inc., Cat. #MK101, Japan). Results were shown in FIG. 1A.

FIG. 1A was a bar diagram of the type I collagen relative expression level of the human skin HS68 fibroblasts after treated with the inactivated bacterial culture solution of different LAB strains in accordance with one embodiment of the present invention. In the embodiment, after the human skin HS68 fibroblasts of the cell models were treated with the 34 testing bacterial strains in vitro, 13 out of 34 strains were found to have the ability to facilitate the type I collagen secretion, which were 1 strain of *Lactobacillus acidophilus*, 1 strain of *Lactobacillus casei*, 5 strains of *Lactobacillus fermentum*, 3 strains of *Lactobacillus paracasei* (including GMNL-653 and other 2 strains), 2 strains of *Lactobacillus plantarum* and 1 strain of *Lactobacillus rhamnosus*, shown in FIG. 1A.

As shown in FIG. 1A, *Lactobacillus paracasei* GMNL-653 had a better ability to stimulate intracellular type I collagen secretion compared to other 12 strains, and thus subsequent assays were assessed using GMNL-653.

3. Analysis of Intracellular Matrix Metalloproteinase-1 (MMP-1) Gene Expression Level of Human Skin Fibroblasts In this embodiment, the HS68 fibroblasts were treated with different concentrations of *Lactobacillus paracasei* GMNL-653. First, the *Lactobacillus paracasei* GMNL-653 cultured overnight was washed twice with sterile water and the cell density was adjusted to $1\times10^{10}$ cells/mL, followed by autoclaving (121° C.) for 15 minutes, and was prepared as inactivated bacterial culture solutions.

The HS68 fibroblasts were cultured in the same way as the second point of Example 1. The difference was that after the HS68 fibroblasts were treated with the inactivated bacterial culture solution for 24 hours, the cell extractions were collected and total RNA extraction, together with reverse transcription reaction, was performed to synthesize cDNA. Methods such as the total RNA extraction and the reverse transcription reaction were known to one of ordinary skills in the art of the present invention rather than repeatedly reciting in detail.

Then, PCR was performed with a pair of primers of SEQ ID NOs: 1 and 2 to quantitatively analyze MMP-1 gene expression level, in which β-actin expression level (using a pair of primers of SEQ ID NOs: 3 and 4) was used as an internal control. The results were shown in FIG. 1B.

Figure 1B:
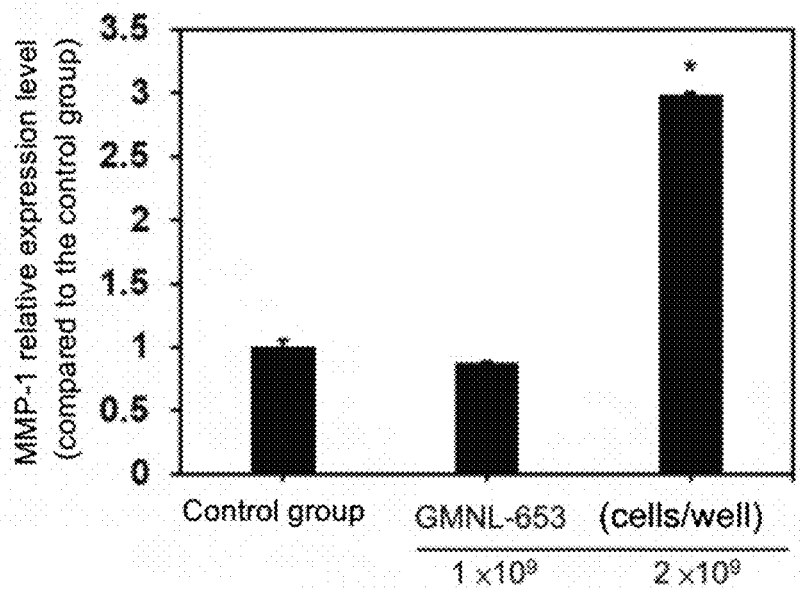
FIG. 1B shows a bar diagram of the MMP-I relative expression level of the human skin HS68 fibroblasts after treated with different concentrations of the inactivated bacterial culture solution of lactic acid bacteria (LAB) strains in accordance with one embodiment of the present invention.

FIG. 1B was a bar diagram of MMP-I relative expression level of the human skin HS68 fibroblasts after treated with the inactivated bacterial culture solution of different lactic acid bacteria (LAB) strains in accordance with one embodiment of the present invention, in which the symbol "*" denoted that the experimental group was found to be significantly different ($p<0.05$) from the control group after analyzed by Student's t-test.

As shown in FIG. 1B, the inactivated culture of *Lactobacillus paracasei* GMNL-653 could facilitate MMP-1 gene expression level, and there was a statistically significant difference in MMP-1 gene expression level between the control group and the experimental group.

Example 2: Assessing Efficacy of *Lactobacillus paracasei* GMNL-653 in Facilitating Wound Healing and Reducing Scars 1. Preparing Inactivated Bacterial Culture-Containing Gel

*Lactobacillus paracasei* GMNL-653 was cultured overnight, washed twice with sterile water, adjusted to a cell density of $2\times10^{10}$ cells/mL and autoclaved (121° C.) for 15 minutes to prepare the inactivated bacterial culture. Then, the inactivated culture of *Lactobacillus paracasei* GMNL-653 was blended in a gel (including 2% of xanthan gum, 6% of xylitol, 4% of trehalose, 10% of glycerol and sterile ultrapure water), and the cell density of the inactivated bacterial culture was adjusted to $1\times10^{10}$ cells/g gel. A control group gel has the same formula without the inactivated bacterial culture.

2. Establishing Animal Testing Model

Eight-week-old BALB/c mice (purchased from BioLASCO, Nangang, Taipei, Taiwan) were anesthetized and tested by a reflex test to ensure the mice were deeply anesthetized for subsequent experiments. First, a wound about 0.2×1 cm was created on a mouse tail about 1 cm away from a proximal end of the tail, and the wound was covered with 0.01 g of the inactivated bacterial culture-containing gel (in which an amount of inactivated cells were $1\times10^{10}$ cells/g gel) or the control group gel, so that the dosage covered on the wound was equal to about $1\times10^8$ cells for each mouse. To make the gel fully absorbed, the wound was exposed to the gel for 15 to 20 minutes (the mice were under anesthesia). The gel was applied daily to the wound in the same way for five days, and recovery conditions of wounds were observed and photographed every 2 to 7 days. The wound area was calculated by an image processing program, Image J, followed by statistical analysis. The results were shown in FIGS. 2A and 2B.

Figure 2A:
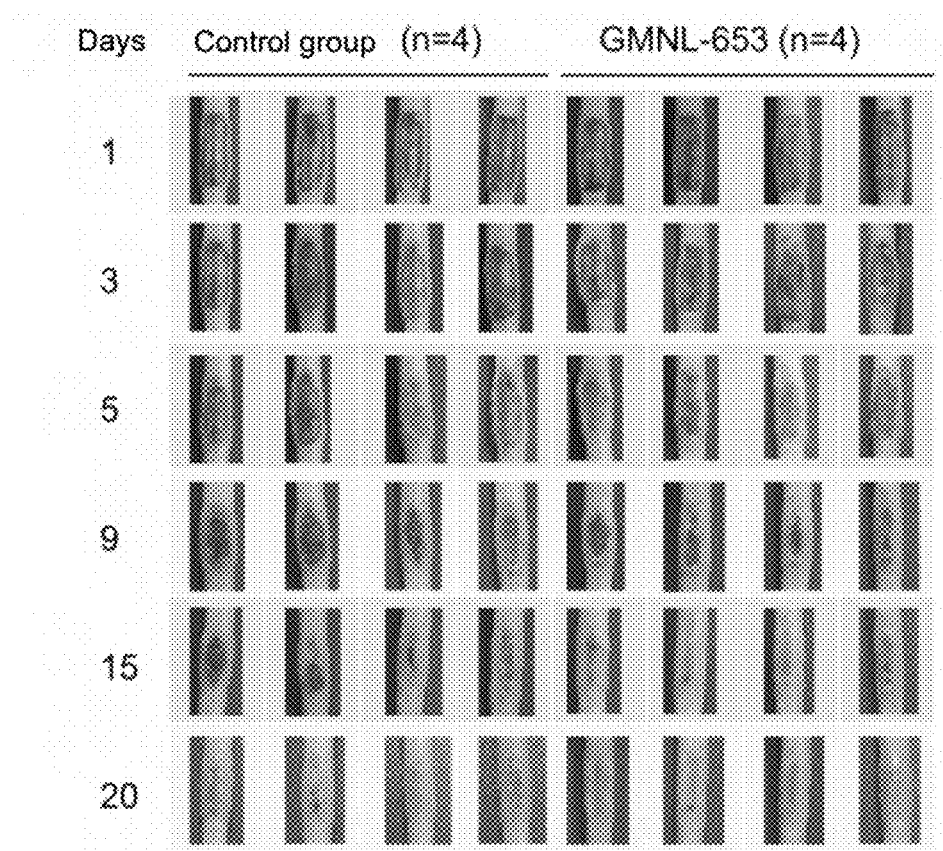
FIGS. 2A and 2B show the appearance (FIG. 2A) and the curve diagram of the wound area (FIG. 2B) of the mice wound covered with the gel containing the inactivated culture of lactic acid bacteria (LAB) in accordance with one embodiment of the present invention.
Figure 2B:
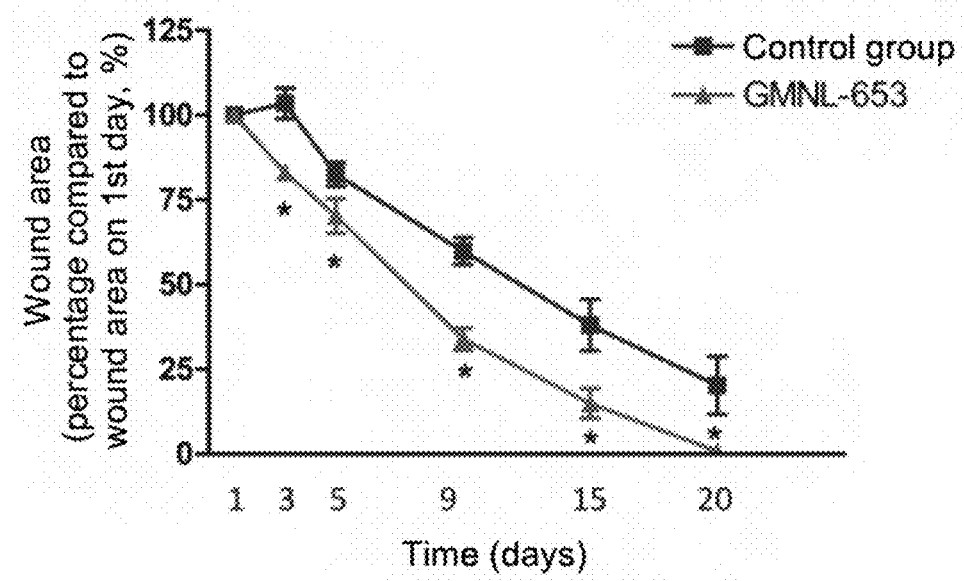

FIGS. 2A and 2B showed the appearance (FIG. 2A) and the curve diagram of the wound area (FIG. 2B) of the mice wound covered with the gel containing the inactivated culture of lactic acid bacteria (LAB) in accordance with one embodiment of the present invention. In FIG. 2B, the wound healing effect was evaluated according to the wound area compared to those on the first day considered as 100%, in which the symbol "*" denoted that the experimental group was significantly different from the control group ($p<0.05$) after analyzed by Student's t-test (n=4).

Referring to FIGS. 2A and 2B, the healing rate in a mouse tail wound covered with the gel containing the inactivated culture of *Lactobacillus paracasei* GMNL-653 was faster than that of the control group. There was a statistically significant difference in the wound healing rate from the third day, and the difference was more significant from the ninth day to the 20th day, the last day of observation.

Moreover, on the 20th day, compared to the control group, of which an obvious scar was formed after wound healing, the mouse tail wounds covered with the gel containing the inactivated culture of *Lactobacillus paracasei* GMNL-653 were flatter, and the scars were thinner, as shown in FIG. 2A, indicating that the inactivated culture of *Lactobacillus paracasei* GMNL-653 could indeed reduce scars.

3. Histological Staining Techniques

Tissue samples on the 5th day to the 9th day in the area of the aforementioned mouse tail wounds were collected, fixed, embedded, sectioned, and stained with hematoxylin & eosin (HE) staining. The results were shown in FIG. 3A. Methods such as fixing, embedding, sectioning, and HE staining were known to one of ordinary skills in the art of the present invention rather than repeatedly reciting in detail.

Furthermore, the changes in distance of the mouse tail wound were measured by Image J software, in which the distances of the wound were defined as distances between two opposite and entire hair follicles closest to the longitudinal ends of the wound edge. The results were shown in FIG. 3B.

Figure 3A:
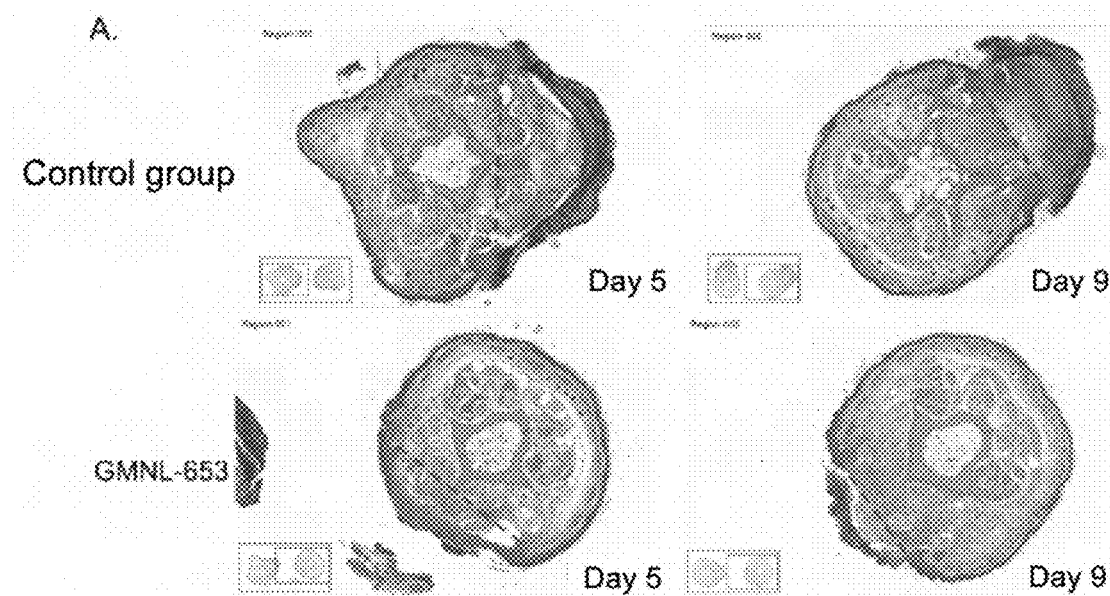
FIGS. 3A and 3B show the histological staining results (FIG. 3A) and the bar diagram of the wound distance change (FIG. 3B) of the mice wound applied with the gel containing the inactivated culture of lactic acid bacteria (LAB) in accordance with one embodiment of the present invention.
Figure 3B:
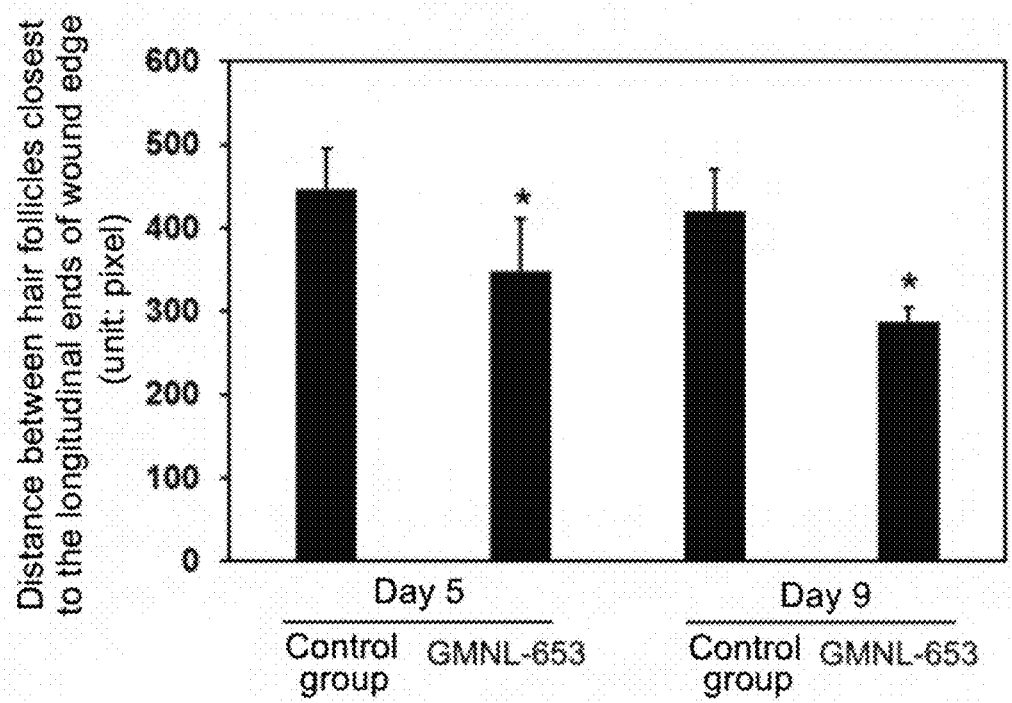

FIGS. 3A and 3B showed the histological staining results (FIG. 3A) and the bar diagram of the wound distance change (unit: pixels; FIG. 3B) of the mice wound applied with the gel containing the inactivated culture of lactic acid bacteria (LAB) in accordance with one embodiment of the present invention. The symbol "*" in FIG. 3B denoted that the experimental group and the control group had a statistically significant difference ($p<0.05$) analyzed by the Student's t-test.

According to the results shown in FIGS. 3A and 3B, the distance of the mouse tail wound significantly decreased either on the fifth day or on the ninth day, indicating that the inactivated culture of *Lactobacillus paracasei* GMNL-653 could indeed accelerate wound healing.

Example 3: Assessing Mechanism of *Lactobacillus paracasei* GMNL-653 in Facilitating Wound Healing 1. Immunohistochemistry Staining (I)

In this embodiment, the tissue samples in the area of the mouse tail wound of the fifth day and the ninth day in Example 2 were collected, fixed, embedded, sectioned, and underwent immunohistochemistry staining for wound healing-related factors, including MMP-1, Masson's trichrome for collagen, type I collagen I(COL1A1), α-SMA and HE staining. The results were shown in FIGS. 4A and 4B. All related sections and immunohistochemistry staining were appointed to AllBio science, Inc., Taichung, Taiwan, and the experimental data were practiced by professionals. Information of antibodies for detecting MMP-1, COL1A1 and α-SMA was shown in TABLE 1.

TABLE 1

| Antibody Name | Manufacturer | #Cat. | Host species |
| --- | --- | --- | --- |
| Human MMP-1 (hMMP1) antibody (clone 41-1E5) | EMD Millipore Corporation, 28820, USA | MAB3307 | Mouse monoclonal antibody |
| COL1A1 antibody (H-197) | Santa Cruz Biotechnology, Inc., USA | sc-28657 | Rabbit polyclonal antibody |
| α-SMA antibody (1A4) | Santa Cruz Biotechnology, Inc., USA | sc-32251 | Mouse monoclonal antibody |

Figure 4A:
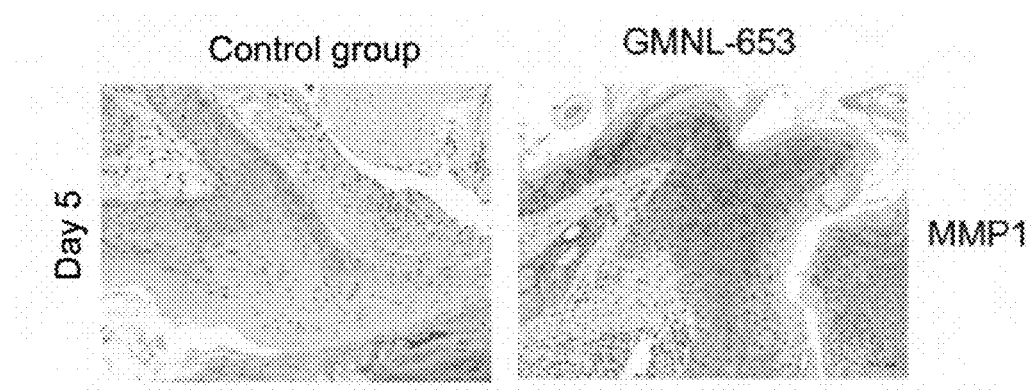
FIGS. 4A and 4B show the immunohistochemistry staining results of the mice wound applied with the gel containing the inactivated culture of lactic acid bacteria (LAB) in accordance with one embodiment of the present invention.
Figure 4B:
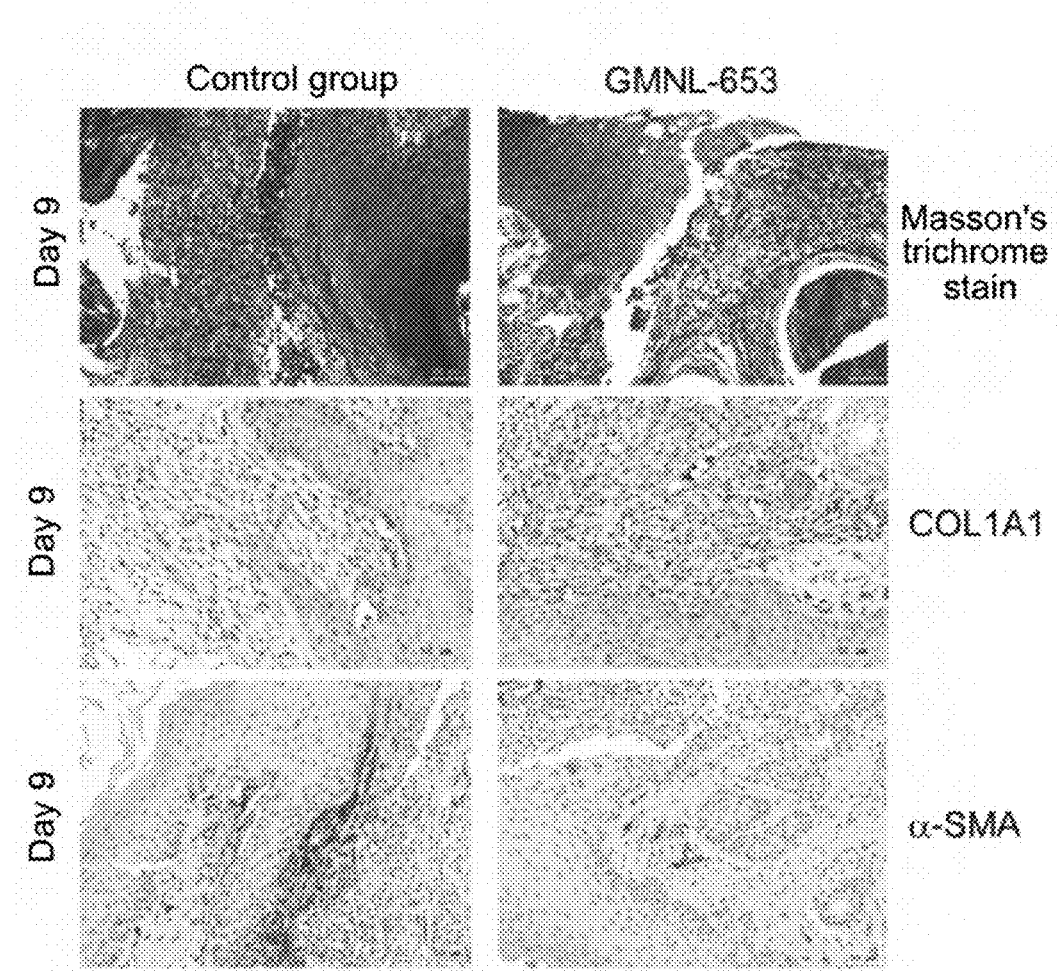

FIGS. 4A and 4B showed the immunohistochemistry staining results of the mouse tail wound applied with the gel containing the inactivated culture of lactic acid bacteria (LAB) in accordance with one embodiment of the present invention.

As shown in FIGS. 4A and 4B, the mouse tail wound covered with the gel containing the inactivated bacterial culture was found to contain more MMP-1 in an early stage (the fifth day) compared to that of the control group, indicating that the inactivated culture of *Lactobacillus paracasei* GMNL-653 could accelerate the complete wound healing by promoting the MMP-1 expression. In the late stage of wound healing (the ninth day), the inactivated culture of *Lactobacillus paracasei* GMNL-653 could promote the overexpression of collagen matrix and type I collagen so as to accelerate complete wound healing.

α-SMA was an indicator for a myofibroblast activation. A previous study showed that excessive scar formations could be prevented by balancing transformations of fibroblasts into myofibroblasts. However, excessive scars formed due to excessive myofibroblast activation. As shown in FIG. 4B, in the late stage of wound healing (the ninth day), the α-SMA expression of the wound covered with the gel containing the inactivated culture of *Lactobacillus paracasei* GMNL-653 was decreased compared to that of the control group, indicating that the inactivated culture of *Lactobacillus paracasei* GMNL-653 could effectively prevent the excessive myofibroblast activation and further the excessive scar formation.

2. Immunohistochemistry Staining (II)

In the embodiment, the mechanism of *Lactobacillus paracasei* GMNL-653 in facilitating wound healing was analyzed using a cell model. TGF-β was an important factor to activate myofibroblasts. However, overexpression of TGF-β led to excessive myofibroblast activation and thus scar formation.

After overnight culture, Lactobacillus. paracasei GMNL-653 was washed twice with sterile water, adjusted to a cell density of 1×10$^{10}$ cells/mL and then autoclaved (121° C.) for 15 minutes, thereby prepared as the inactivated bacterial culture solutions. The HS68 fibroblasts were cultured in the same way as the second point of Example 1. The difference was that when the HS68 fibroblasts were continuously cultured in the serum-free culture medium, the HS68 fibroblasts were treated with TGF-β (20 ng/mL) and the inactivated bacterial culture solutions (1×10$^9$ cells/well or 2×10$^9$ cells/well) for 24 hours. After that, the cell extractions were collected, and proteins were extracted, followed by a protein level analysis with Western blotting for α-SMA, Smad 2/3, phospho-Smad (p-Smad 2) and a housekeeping gene (glyceraldehyde 3-phosphate dehydrogenase, GAPDH, as the internal control). The results were shown in FIG. 5.

Methods such as protein extraction and Western blotting were known to one of ordinary skills in the art of the present invention rather than repeatedly reciting in detail. The information of the antibodies used to detect α-SMA, Smad 2/3, p-Smad 2 and GAPDH was shown in TABLE 2.

TABLE 2

| Antibody Name | Manufacturer | #Cat. | Host species |
|---|---|---|---|
| α-SMA antibody (1A4) | Santa Cruz Biotechnology, Inc., USA | sc-32251 | Mouse monoclonal antibody |
| Smad 2/3 antibody (clone C4T) | EMD Millipore Corporation, USA | 04-914 | Rabbit monoclonal antibody |
| p-Smad 2 antibody (Ser 465/467, clone A5S) | EMD Millipore Corporation, USA | 04-953 | Rabbit monoclonal antibody |
| GAPDH antibody | GeneTex International Corporation, Taiwan | GTX100118 | Rabbit polyclonal antibody |

Figure 5:
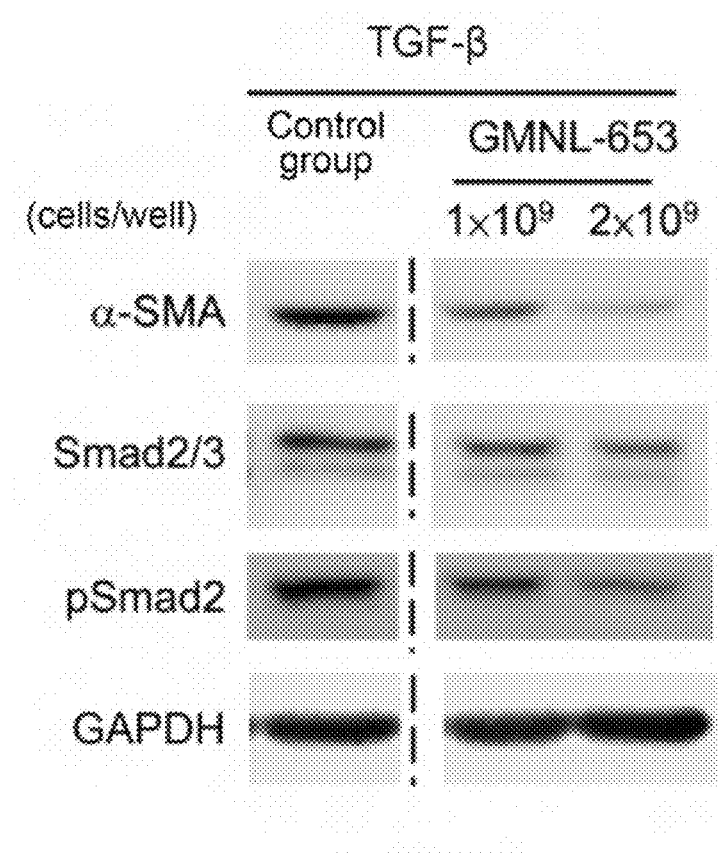
FIG. 5 shows the Western blot analyzing result of the inhibited TGF-β-induced α-SMA expression pathway in vitro by the inactivated culture of *Lactobacillus* sp. in accordance with one embodiment of the present invention.

FIG. 5 showed the Western blot analysis result of the inhibited TGF-β-induced α-SMA expression pathway in vitro by the inactivated culture of Lactobacillus sp. in accordance with one embodiment of the present invention.

As shown in FIG. 5, the inactivated culture of Lactobacillus paracasei GMNL-653 could affect the downstream of α-SMA expression by inhibiting TGF-β-induced p-Smad 2. In other words, the inactivated culture of Lactobacillus paracasei GMNL-653 could achieve the purpose of inhibiting the scar formation via inhibiting TGF-β-induced α-SMA expression route.

It should be supplemented that, the present invention used the inactivated culture of Lactobacillus paracasei GMNL-653 as the effective ingredient could indeed accelerate wound healing, decrease the chance for pathogens to infect human body and also reducing scars, in which the mechanism could promote the production of MMP-1 in the early stage and the collagen secretion in the middle stage and the late stage of wound healing to accelerate wound healing. Moreover, in vitro assays also proved that the inactivated culture of Lactobacillus paracasei GMNL-653 could reduce the formation of scars by inhibiting TGF-6-induced p-Smad 2 and the α-SMA overexpression. Furthermore, since Lactobacillus paracasei GMNL-653 was in a dosage form of inactivated bacterial culture, the related products applying the present invention had less viable cell count problems and deterioration problems. In addition, the stability of the product could be controlled more easily. Thus, the present invention could be applied in more fields and had the potential to be applied for the method of facilitating wound healing and reducing scars.

In summary, although uses of the topical composition and the pharmaceutical composition for facilitating wound healing and scar reduction are illustrated by using specific stains, specific dosage forms, specific subjects, specific methods of administration or specific methods of evaluations as examples in the present invention, any one of ordinary skills in the art of the present invention can realize that the present invention was not limited thereto, and the present invention can also be implemented by using other strains, dosage forms or other subjects, other administration or other methods for evaluating without departing from the spirit and scope of the present invention.

It can be known from the aforementioned embodiments that, the topical composition and the pharmaceutical composition of the present invention have the advantage that the effective dosage is the inactivated culture of Lactobacillus paracasei GMNL-653, which has excellent stability and is safe without viable cell count problems and deterioration concerns. Moreover, the inactivated culture of Lactobacillus paracasei GMNL-653 can significantly facilitate wound healing and reduce scars, thereby can be applied in the method of facilitating wound healing and reducing scars.

Although the present invention has been disclosed in several embodiments as mentioned above, these embodiments do not intend to limit the present invention. Various changes and modifications can be made by any one of ordinary skills in the art to which the present invention pertains, without departing from the spirit and scope of the present invention. Therefore, the claimed scope of the present invention shall be defined by the appended claims.

What is claimed is:

1. A method of facilitating wound healing and reducing scars comprising contacting the wound with a pharmaceutical composition comprising an effective dosage of an inactivated culture of *Lactobacillus* sp., wherein the inactivated culture of *Lactobacillus* sp. is obtained by culturing and sterilizing *Lactobacillus paracasei* GMNL-653 deposited with an accession number of CCTCC M2016226 on Apr. 25, 2016 in China Center for Type Culture Collection (CCTCC), Wuhan University, Wuhan 430072, China and comprises an inactivated bacterial culture solution or a bacterial lyophilized powder.

2. The method of facilitating wound healing and reducing scars of claim 1 wherein the effective dosage is $1 \times 10^9$ cells/mL to $1 \times 10^{10}$ cells/mL.

3. The method of facilitating wound healing and reducing scars of claim 1 wherein the pharmaceutical composition is a dosage form selected from the group consisting of a gel, a gel dressing, a spongy dressing, a film dressing or any combination thereof.

* * * * *

SEQUENCE LISTING

<160> NUMBER OF SEQ ID NOS: 4

<210> SEQ ID NO 1
<211> LENGTH: 20
<212> TYPE: DNA
<213> ORGANISM: Artificial sequence
<220> FEATURE:
<223> OTHER INFORMATION: MMP-1 gene forward primer

<400> SEQUENCE: 1
tgctcatgct tttcaaccag                    20

```
<210> SEQ ID NO 2
<211> LENGTH: 20
<212> TYPE: DNA
<213> ORGANISM: Artificial sequence
<220> FEATURE:
<223> OTHER INFORMATION: MMP-1 gene reverse primer

<400> SEQUENCE: 2
ggtacatcaa agccccgata                                              20

<210> SEQ ID NO 3
<211> LENGTH: 20
<212> TYPE: DNA
<213> ORGANISM: Artificial sequence
<220> FEATURE:
<223> OTHER INFORMATION: Beta-actin gene forward primer

<400> SEQUENCE: 3
tccctggaga agagctacga                                              20

<210> SEQ ID NO 4
<211> LENGTH: 20
<212> TYPE: DNA
<213> ORGANISM: Artificial sequence
<220> FEATURE:
<223> OTHER INFORMATION: Beta-actin gene reverse primer

<400> SEQUENCE: 4
agcactgtgt tggcgtacag                                              20
```